US011399785B2

(12) United States Patent
Ohara

(10) Patent No.: US 11,399,785 B2
(45) Date of Patent: Aug. 2, 2022

(54) RADIATION IMAGING SYSTEM AND IMAGING GUIDE PATTERN SELECTION DEVICE

(71) Applicant: Konica Minolta, Inc., Tokyo (JP)

(72) Inventor: Hiromu Ohara, Tokyo (JP)

(73) Assignee: KONICA MINOLTA, INC., Tokyo (JP)

( * ) Notice: Subject to any disclaimer, the term of this patent is extended or adjusted under 35 U.S.C. 154(b) by 527 days.

(21) Appl. No.: 16/401,640

(22) Filed: May 2, 2019

(65) Prior Publication Data
US 2019/0357866 A1    Nov. 28, 2019

(30) Foreign Application Priority Data

May 24, 2018    (JP) .............................. JP2018-099252

(51) Int. Cl.
*A61B 6/00* (2006.01)
*G09B 19/04* (2006.01)
*G09B 19/00* (2006.01)

(52) U.S. Cl.
CPC ................ *A61B 6/461* (2013.01); *A61B 6/46* (2013.01); *A61B 6/465* (2013.01); *A61B 6/5294* (2013.01); *A61B 6/541* (2013.01); *A61B 6/542* (2013.01); *G09B 19/04* (2013.01); *G09B 19/003* (2013.01)

(58) Field of Classification Search
CPC .......... A61B 6/461; A61B 6/465; A61B 6/46; A61B 6/5294; A61B 6/542; A61B 6/541; A61B 6/527; A61B 6/50; A61B 6/548; A61B 6/566; G09B 19/04; G09B 19/003; G16H 30/00
See application file for complete search history.

(56) References Cited

U.S. PATENT DOCUMENTS

| 7,769,430 B2* | 8/2010 | Mostafavi | A61B 6/541 600/428 |
| 2004/0082845 A1* | 4/2004 | Matsumoto | G16H 50/20 600/407 |
| 2005/0244044 A1* | 11/2005 | Inoue | G06T 7/0012 382/132 |
| 2007/0214017 A1* | 9/2007 | Profio | G16H 30/20 705/3 |

(Continued)

FOREIGN PATENT DOCUMENTS

| JP | 2005-312776 A | 11/2005 |
| JP | 2012-130612 A | 7/2012 |
| JP | 2012130612 A * | 7/2012 |

*Primary Examiner* — Sean D Mattson
(74) *Attorney, Agent, or Firm* — Lucas & Mercanti, LLP

(57) ABSTRACT

A radiation imaging system including an imager that performs imaging of moving images by irradiating a subject with radiation, the radiation imaging system including
a storage in which an imaging guide pattern for instructing a predetermined motion to the subject at a time of imaging by the imager is associated with a predetermined word that can be included in an imaging order and is stored,
a hardware processor that acquires an imaging order to imaging by the imager, extracts the predetermined word from the acquired imaging order, and selects an imaging guide pattern that is associated with the extracted predetermined word from imaging guide patterns stored in the storage, and
an instructor that instructs the predetermined motion to the subject, based on the selected imaging guide pattern.

9 Claims, 8 Drawing Sheets

(56) References Cited

U.S. PATENT DOCUMENTS

| | | | |
|---|---|---|---|
| 2008/0089463 A1* | 4/2008 | Nakamura | A61B 6/541 378/4 |
| 2008/0097747 A1* | 4/2008 | Stonefield | A61B 5/7405 704/9 |
| 2012/0183191 A1* | 7/2012 | Nakamura | A61B 5/416 382/128 |
| 2016/0192894 A1* | 7/2016 | Ohishi | A61B 6/504 715/771 |
| 2017/0020470 A1* | 1/2017 | Tezuka | A61B 6/542 |

* cited by examiner

FIG.3

| CLASSIFICATION | IMAGING ORDER WORD | IMAGING GUIDE PATTERN | ANALYSIS CONTENT |
|---|---|---|---|
| DISEASE | LUNG CANCER | QUIET BREATHING | WITHOUT ANALYSIS (ONLY MOVING IMAGE) |
| | COPD | DEEP BREATHING | VENTILATION ANALYSIS+ THORACIC DIAPHRAGM MOVING AMOUNT MEASUREMENT |
| | PULMONARY EMBOLISM | BREATH HOLDING (INHALING) | BLOOD FLOW ANALYSIS |
| BREATHING PATTERN | QUIET BREATHING | QUIET BREATHING | WITHOUT ANALYSIS (ONLY MOVING IMAGE) |
| | DEEP BREATHING | DEEP BREATHING | VENTILATION ANALYSIS+ THORACIC DIAPHRAGM MOVING AMOUNT MEASUREMENT |
| | BREATH HOLDING (INHALING) | BREATH HOLDING (INHALING) | BLOOD FLOW ANALYSIS |
| | BREATH HOLDING (EXHALING) | BREATH HOLDING (EXHALING) | BLOOD FLOW ANALYSIS (SPECIAL) |
| ANALYSIS | VENTILATION ANALYSIS | DEEP BREATHING | VENTILATION ANALYSIS |
| | BLOOD FLOW ANALYSIS | BREATH HOLDING (INHALING) | BLOOD FLOW ANALYSIS |
| | THORACIC DIAPHRAGM MOVING AMOUNT MEASUREMENT | DEEP BREATHING | THORACIC DIAPHRAGM MOVING AMOUNT MEASUREMENT |
| ORTHOPEDIC FIELD | TEMPOROMANDIBULAR JOINT | TEMPOROMANDIBULAR JOINT | TRACKING INCISOR MOVING DISTANCE IN TIME |
| | KNEE JOINT | KNEE JOINT | MOVING DISTANCE OF CONTACT POINT OF BENT PORTION AND LATERAL CONDYLE OF FEMUR IN EXTENSION OF KNEE JOINT AND SUPERIOR ARTICULAR SURFACE OF TIBIA |
| | CERVICAL SPINE | CERVICAL SPINE | ANALYZING ARRANGEMENT OF VERTEBRAL BODY IN FORWARD AND BACKWARD BENDING MOVEMENT OF CERVICAL SPINE (CERVICAL SPINE ALIGNMENT) IN TIME SERIES |
| | WRIST | WRIST | WITHOUT ANALYSIS (ONLY MOVING IMAGE) |

FIG.4

| IMAGING GUIDE PATTERN | VOICE OUTPUT EXAMPLE |
|---|---|
| DEEP BREATHING | BREATHE IN DEEPLY, BREATHE IN, BREATHE IN, BREATHE IN, BREATHE IN, HOLD YOUR BREATH, BREATHE OUT SLOWLY, BREATHE OUT, BREATHE OUT, BREATHE OUT, BREATHE OUT, BREATHE OUT COMPLETELY TO THE END, HOLD YOUR BREATH, OK, IMAGING IS OVER. |
| QUIET BREATHING | IMAGING IS STARTED. BREATHE AS USUAL. (SILENT: FOR EXAMPLE, ABOUT 15 SECONDS) OK, IMAGING IS OVER. |
| BREATH HOLDING (INHALING) | BREATHE LIGHTLY, HOLD YOUR BREATH, (SILENT: FOR EXAMPLE, ABOUT 8 SECONDS) OK, IMAGING IS OVER |
| TEMPOROMANDIBULAR JOINT | OPEN YOUR MOUTH WIDE SLOWLY, CLOSE YOUR MOUTH SLOWLY, OK, IMAGING IS OVER. |
| KNEE JOINT | BEND YOUR KNEE SLOWLY, STRETCH YOUR KNEE SLOWLY, OK, IMAGING IS OVER. |
| CERVICAL SPINE | BEND YOUR NECK FORWARD SLOWLY, STRETCH YOUR NECK BACKWARD SLOWLY, OK, IMAGING IS OVER. |
| WRIST | TWIST YOUR WRIST RIGHTWARD SLOWLY, TWIST YOUR WRIST LEFTWARD SLOWLY, OK IMAGING IS OVER. |

FIG.5

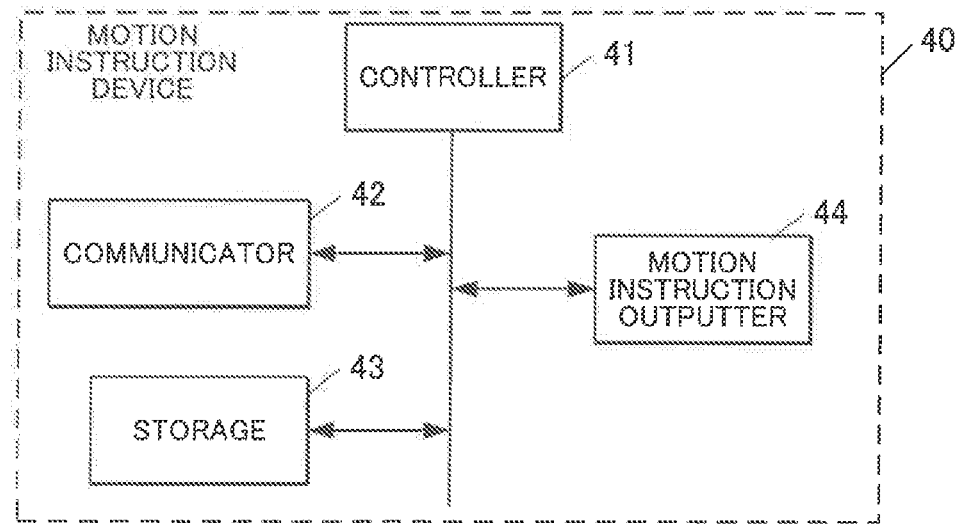

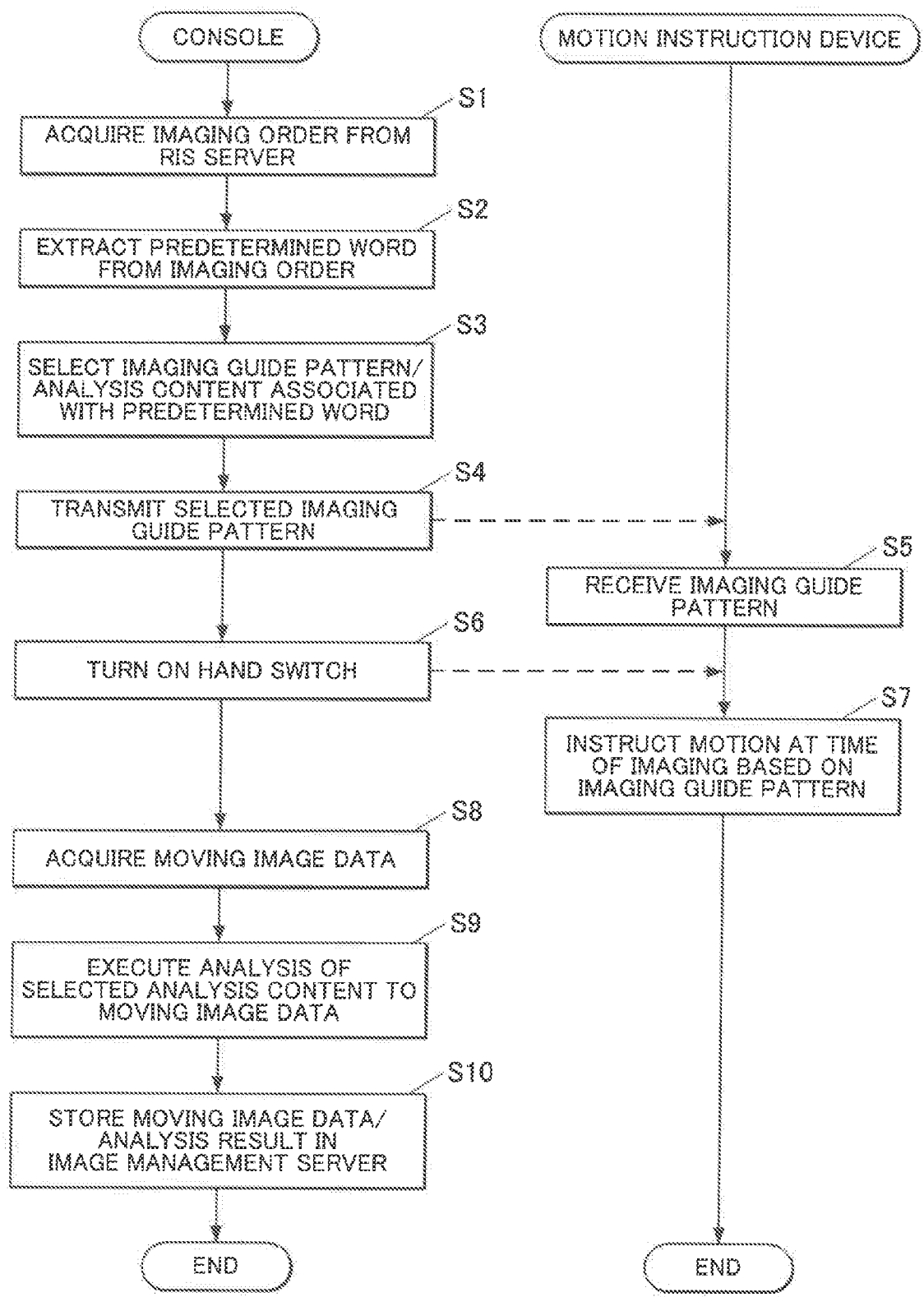

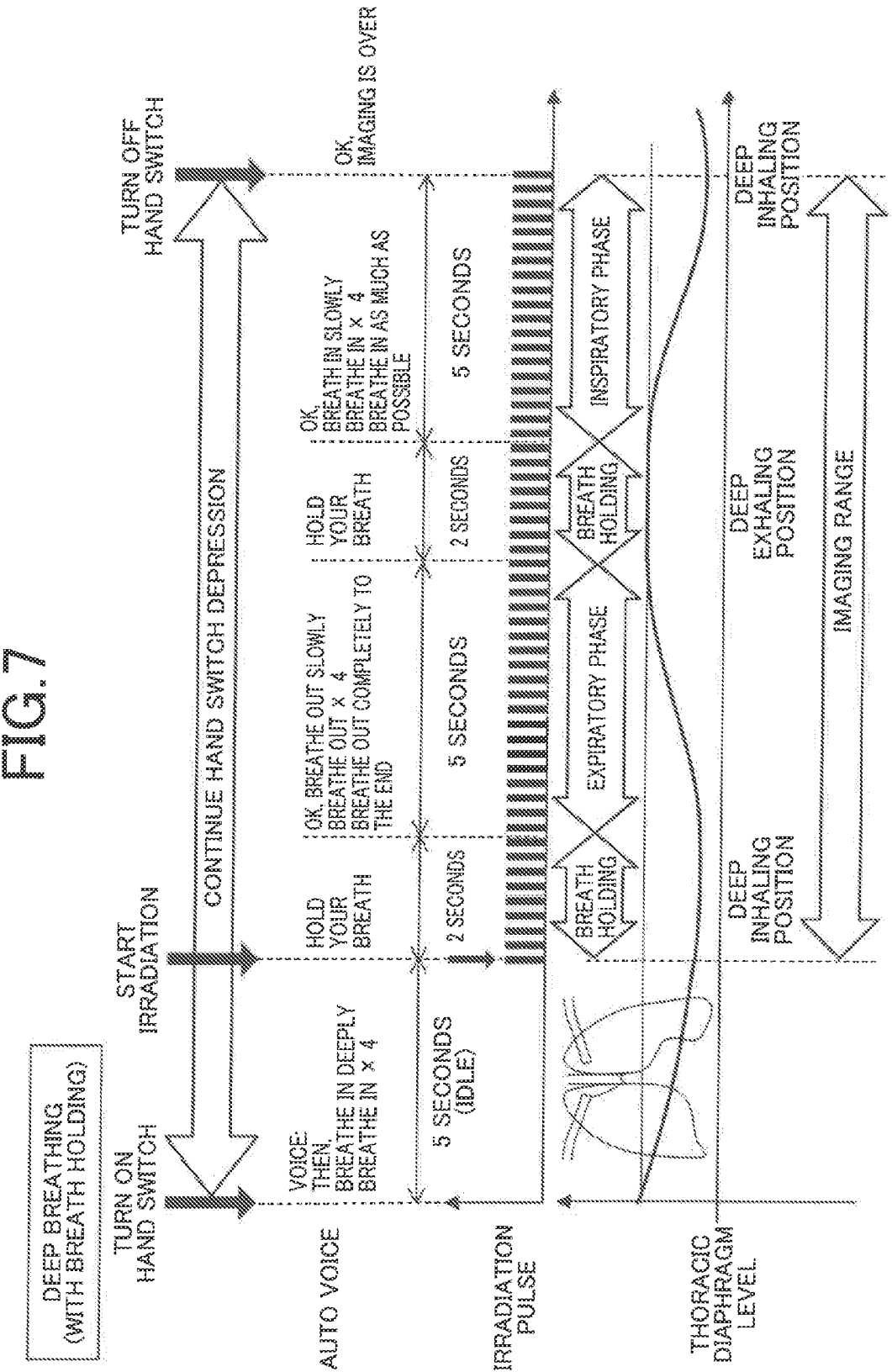

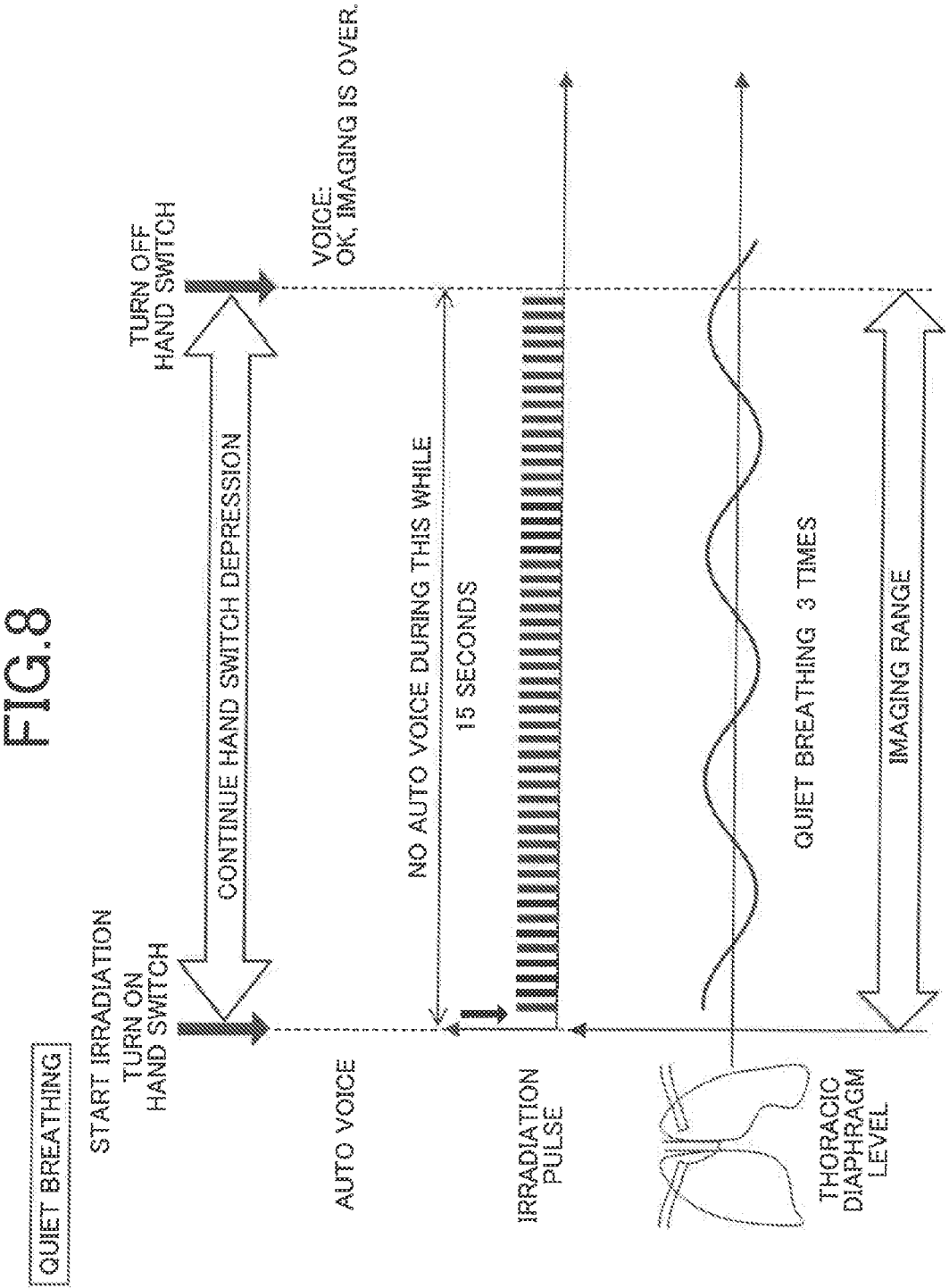

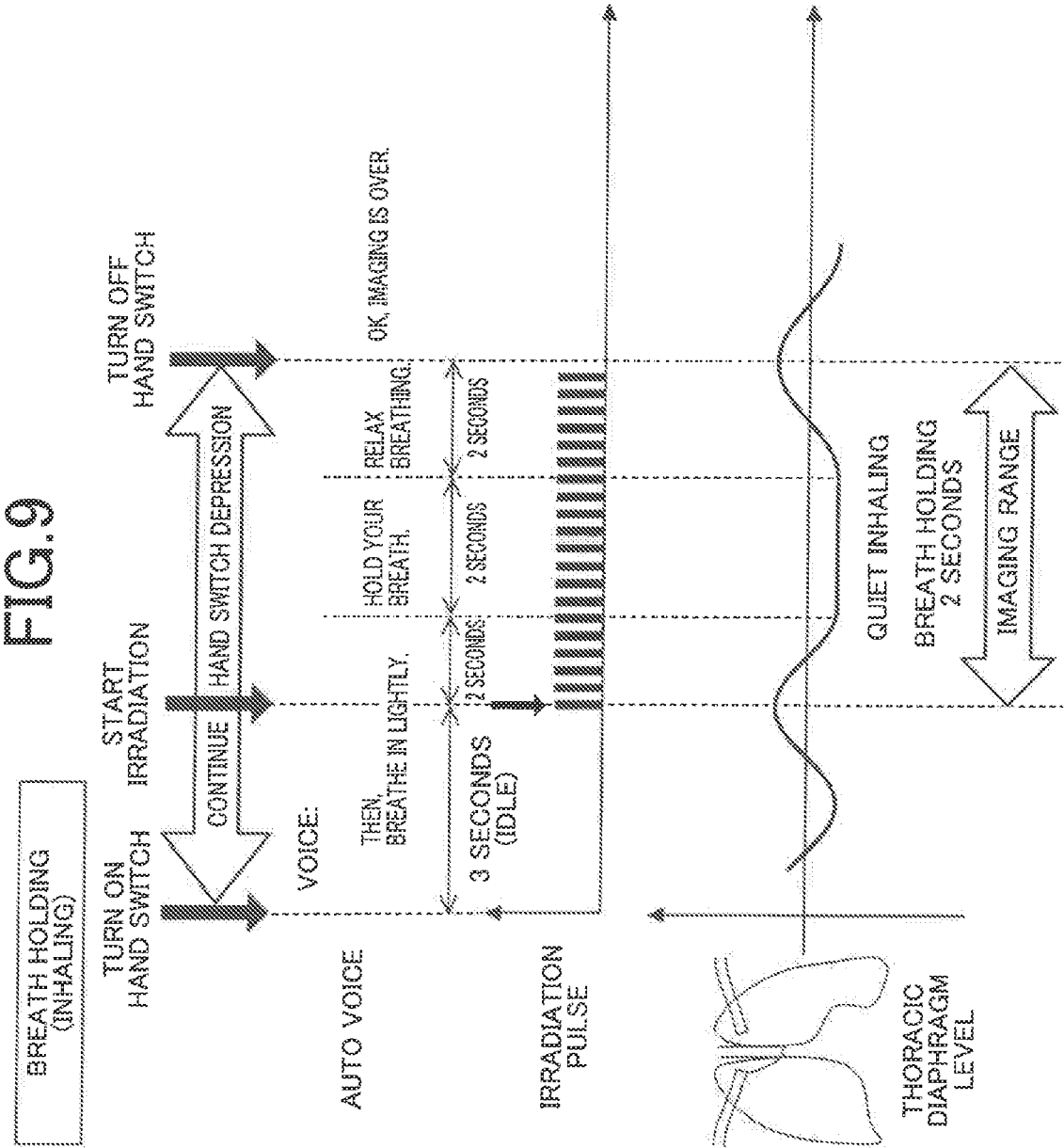

RADIATION IMAGING SYSTEM AND IMAGING GUIDE PATTERN SELECTION DEVICE

BACKGROUND

Technological Field

The present invention relates to a radiation imaging system and an imaging guide pattern selection device.

Description of the Related Art

In a radiation imaging system that irradiates a subject with radiation and performs imaging of moving images, imaging is performed while a motion instruction is given to the subject at a proper timing. For example, in order to cause the subject to perform breathing motion at a predetermined timing, a voice generating device (auto voice) or the like is used.

Further, there is provided a breathing timing notifying device including a plurality of kinds of breathing timing notifiers that notify a subject of breathing timings, a selector that selects at least one breathing timing notifier, and a controller that drives the breathing timing notifier that is selected by the selector (refer to Japanese Patent Laid-Open No. 2012-130612).

Further, there is proposed a radiation image acquiring device including acquiring means that acquires continuous radiation images based on the intensity distribution of radiation transmitted through a subject, extraction means that extracts lung field parts from the respective continuous radiation images, and determination means that detects a fluctuation state from the lung field parts, and determines whether or not a breathing state of the subject is suitable for imaging a dynamic state of breathing, based on the detected fluctuation state (refer to Japanese Patent Laid-Open No. 2005-312776).

However, an imaging guide pattern for instructing a predetermined motion to a subject at the time of imaging moving images differs depending on the disease, and therefore, there is a possibility that if a radiographer erroneously selects the imaging guide pattern, imaging intended by a doctor is not performed.

SUMMARY

The present invention is made in the light of the above described problem in the conventional art, and has an object to prevent erroneous selection of an imaging guide pattern, and achieve imaging of moving images intended by a doctor.

To achieve at least one of the abovementioned objects, according to a first aspect of the present invention, a radiation imaging system reflecting one aspect of the present invention is a radiation imaging system including an imager that performs imaging of moving images by irradiating a subject with radiation, and includes a storage in which an imaging guide pattern for instructing a predetermined motion to the subject at a time of imaging by the imager is associated with a predetermined word that can be included in an imaging order and is stored;

a hardware processor that acquires an imaging order to imaging by the imager, extracts the predetermined word from the acquired imaging order, and selects an imaging guide pattern that is associated with the extracted predetermined word from imaging guide patterns stored in the storage, and an instructor that instructs the predetermined motion to the subject, based on the selected imaging guide pattern.

According to a second aspect of the present invention, an imaging guide pattern selection device reflecting one aspect of the present invention includes a storage in which an imaging guide pattern for instructing a predetermined motion to a subject at a time of imaging by an imager that performs imaging of a moving image by irradiating the subject with radiation is associated with a predetermined word that can be included in an imaging order and is stored, and a hardware processor that acquires an imaging order to imaging by the imager, extracts the predetermined word from the acquired imaging order, and selects an imaging guide pattern that is associated with the extracted predetermined word from imaging guide patterns stored in the storage.

BRIEF DESCRIPTION OF THE DRAWINGS

The advantages and features provided by one or more embodiments of the invention will become more fully understood from the detailed description given hereinbelow and the appended drawings which are given by way of illustration only, and thus are not intended as a definition of the limits of the present invention.

FIG. 3 is diagram showing a data configuration example of a correspondence table;

FIG. 4 is a diagram showing a voice output example of an imaging guide pattern;

FIG. 5 is a block diagram showing a functional configuration of a motion instruction device;

FIG. 6 is a ladder chart showing an imaging process that is executed in the console and the motion instruction device;

FIG. 7 is a specific example of a breathing pattern at a time of deep breathing (with breath holding);

FIG. 8 is a specific example of a breathing pattern at a time of quiet breathing; and FIG. 9 is a specific example of a breathing pattern at a time of breath holding (inhaling).

DETAILED DESCRIPTION OF EMBODIMENTS

Hereinafter, one or more embodiments of the present invention will be described with reference to the drawings. However, the scope of the invention is not limited to the disclosed embodiments.

[Configuration of Radiation Imaging System]

Figure 1:
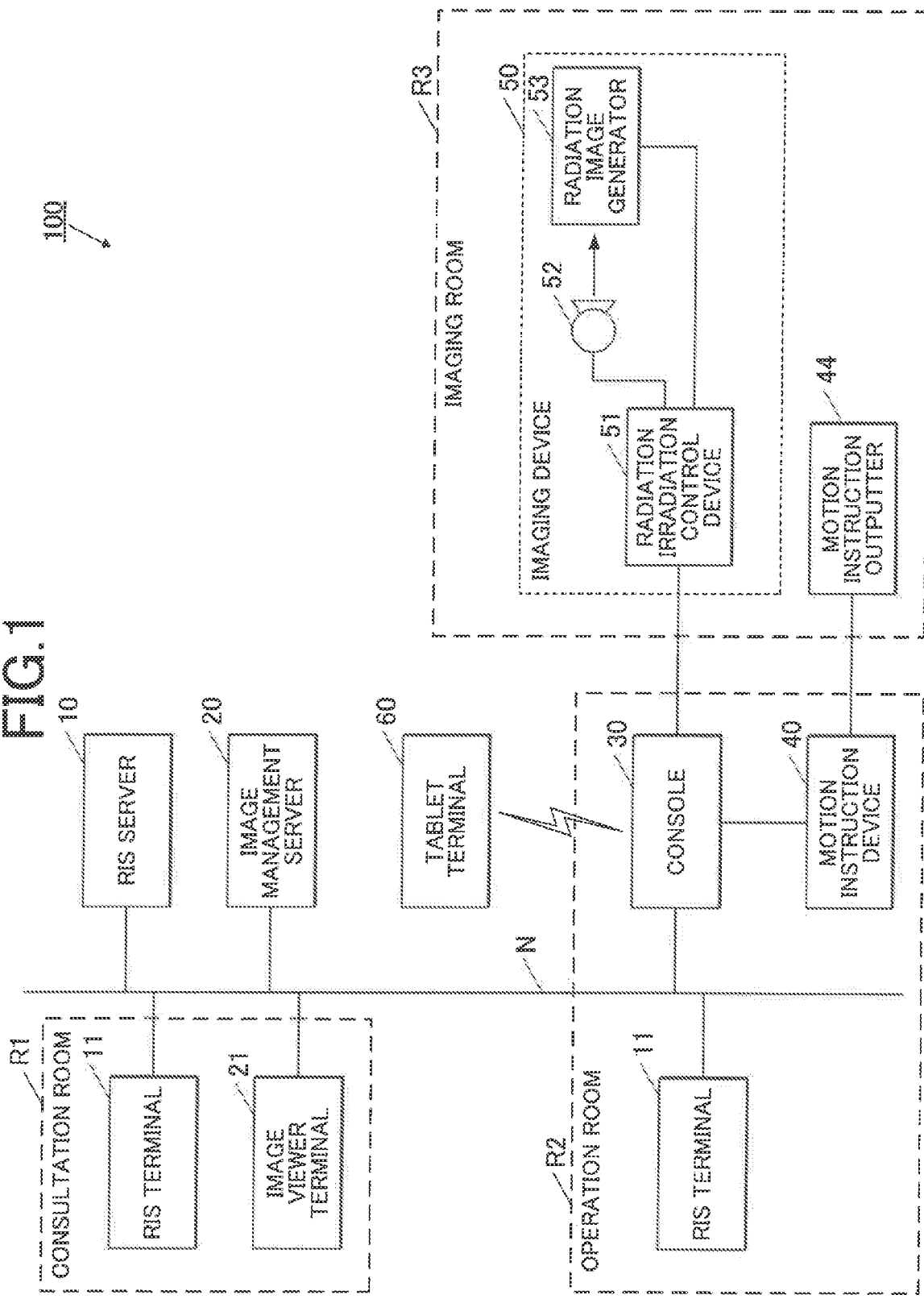
FIG. 1 is an entire configuration diagram of a radiation imaging system in an embodiment of the present invention.

FIG. 1 shows an entire configuration of a radiation imaging system 100.

As shown in FIG. 1, the radiation imaging system 100 includes a RIS (Radiology Information System) server 10, a RIS terminal 11, an image management server 20, an image viewer terminal 21, a console 30, a motion instruction device 40, an imaging device 50, and a tablet terminal 60. The RIS server 10, the RIS terminal 11, the image management server 20, the image viewer terminal 21 and the console 30 are connected so that data communication is possible via a communication network N such as a LAN (Local Area Network) in hospital.

The RIS server 10 manages information in a radiology department, such as reservations of imaging by radiation equipment, and inspection results. The RIS server 10 manages an imaging order issued based on an operation of a doctor in the RIS terminal 11 of a consultation room R1 by associating the imaging order with a patient (subject) to be an object to be imaged and the doctor who requests imaging. The RIS server 10 transmits an imaging order to the console 30 corresponding to the imaging device 50 designated in the imaging order.

The RIS terminal 11 is a computer device installed in a consultation room R1 and an operation room R2, and is used at a time of issuing an imaging order to the RIS server 10, and browsing the information managed by the RIS server 10. The doctor designates imaging of moving images and issues an imaging order, in the RIS terminal 11 of the consultation room R1.

The image management server 20 stores image data of radiation images generated in the imaging device 50, and manages the image data according to patient. The image management server 20 includes a PACS (Picture Archiving and Communication System).

The image viewer terminal 21 is a computer device installed in the consultation room R1, and is used at a time of browsing the radiation images and analysis results managed by the image management server 20, and the like.

The console 30 is installed in the operation room R2, and is connected to the motion instruction device 40 and the imaging device 50 to be communicable by wire or radio. Further, the console 30 is communicable with the tablet terminal 60 by radio. The console 30 is capable of setting various imaging conditions to the imaging device 50 based on the imaging order acquired from the RIS server 10 and the operation by the radiographer. Further, the console 30 selects an imaging guide pattern based on the imaging order, and transmits the selected imaging guide pattern to the motion instruction device 40. The console 30 is an imaging guide pattern selection device that receives the imaging order, and outputs the imaging guide pattern that is associated with a predetermined word included in the imaging order in advance.

The motion instruction device 40 outputs a motion instruction (imaging guide) from a motion instruction outputter 44 installed in an imaging room R3. The motion instruction device 40 instructs to subjects a predetermined motion such as a breathing motion, bending and stretching of an imaging site, and a change of an orientation of the imaging site.

The imaging device 50 is an imager that irradiates a subject with radiation and performs imaging of moving images, and is installed in the imaging room R3. The imaging device 50 images moving images of, for example, dynamic states such as a morphological changes of lung expansion and contraction, movement of a thoracic diaphragm, and heart pulse following a breathing motion. Further, the imaging device 50 images moving images following bending and stretching of the joint of the imaging site and the change of orientation of the imaging site. In imaging of moving images, to the imaging site of a subject, radiation of X-ray or the like is repeatedly irradiated in a pulse form at predetermined time intervals (pulse irradiation), or radiation is irradiated continuously without interruption at a low dose rate (continuous irradiation), and thereby a plurality of images showing the dynamic state of the subject are acquired. A series of images obtained by imaging of moving images is referred to as moving images.

The imaging device 50 includes a radiation irradiation control device 51, a radiation source 52, and a radiation image generator 53.

The radiation irradiation control device 51 is connected to the console 30, controls the radiation source 52 and the radiation image generator 53 based on imaging conditions inputted from the console 30 and performs radiation imaging. The imaging conditions inputted from the console 30 are, for example, a pulse width, a pulse interval, an imaging time per imaging, a value of a tube current, a value of a tube voltage and the like.

The radiation irradiation control device 51 acquires image data of a radiation image generated by the radiation image generator 53, and transmits the image data to the console 30.

The radiation source 52 is disposed in a position facing the radiation image generator 53 with a subject between the radiation source 52 and the radiation image generator 53, and irradiates the subject with radiation in accordance with control of the radiation irradiation control device 51.

The radiation image generator 53 has a substrate where pixels including radiation detection elements that generates electric charges corresponding to a dose by receiving radiation and switch elements that accumulates/releases electric charges are arranged in a two-dimensional shape (matrix shape), and a reading circuit that reads the amount of electric charges released from the respective pixels as signal values, and generates image data from the plurality of signal values read by the reading circuit. The radiation image generator 53 outputs the generated image data to the radiation irradiation control device 51.

Note that the radiation image generator 53 may be of a type (a so-called indirect type) that contains a scintillator or the like, converts radiation which is irradiated into light of another wavelength such as visible light by the scintillator, and generates electric charges corresponding to the converted light, or may be of a type (a so-called direct type) that directly generates electric charges from radiation without using a scintillator or the like.

Further, the radiation image generator 53 may be of an exclusive machine type integrated with an imaging base, or may be of a portable type (cassette type).

The tablet terminal 60 is a portable type computer apparatus including a controller, operation unit, a display, a voice outputter, a communicator, a storage and the like, and is used by a subject. The tablet terminal 60 outputs a motion instruction (imaging guide) for preliminary practice before imaging, based on the imaging guide pattern transmitted from the console 30.

(Configuration of Console)

Figure 2:
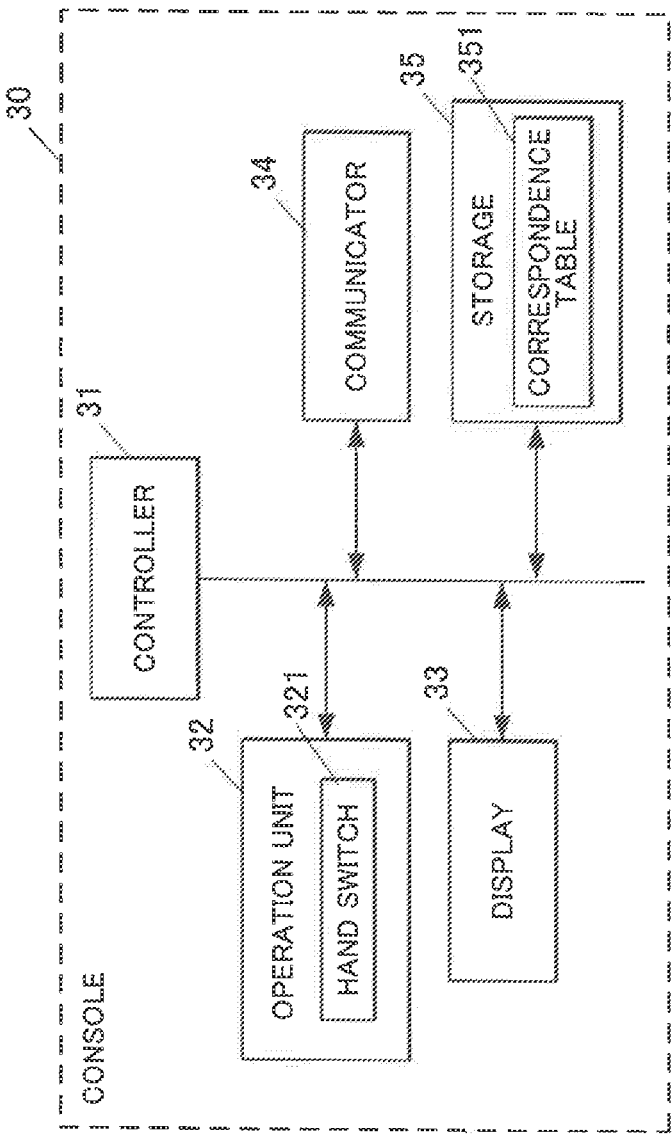
FIG. 2 is a block diagram showing a functional configuration of a console.

FIG. 2 shows a functional configuration of the console 30.

As shown in FIG. 2, the console 30 includes a controller 31, an operation unit 32, a display 33, a communicator 34, and a storage 35.

The controller 31 includes a CPU (Central Processing Unit) and a RAM (Random Access Memory), and generally controls processing operations of the respective components of the console 30. Specifically, the CPU of the controller 31 reads a system program and various processing programs that are stored in the storage 35, in response to the operation of the operation unit 32, and expands the programs in the RAM, and executes various processes in accordance with the expanded programs.

The operation unit 32 includes a keyboard including a cursor key, letter/number input keys, and various function keys, and a pointing device such as a mouse, and outputs operation signals inputted by a key operation to the keyboard and a mouse operation to the controller 31. Further, the operation unit 32 includes a hand switch 321 capable of being pressed in two steps, and outputs a pressed state (OFF/one-step depression (lightly pressed state)/two-step depression (deeply pressed state)) of the hand switch 321 to the controller 31. When the operation unit 32 includes a touch panel stacked on the display screen of the display 33, the operation unit 32 outputs an operation signal corresponding to the position of the touch operation by a finger or the like of an operator to the controller 31.

The display 33 includes a monitor such as an LCD (Liquid Crystal Display), and displays various screens in accordance with an instruction of a display signal received from the controller 31.

The communicator 34 includes a LAN adaptor, a modem, or TA (Terminal Adapter), and performs data communication with various devices connected to the communication network N. Further, the communicator 34 performs data communication with the motion instruction device 40, the imaging device 50 and the tablet terminal 60.

The storage 35 includes a non-volatile semiconductor memory, or a hard disk. The storage 35 stores various programs that are executed in the controller 31, parameters necessary to execute the process by the programs, and data of processing results and the like. For example, a correspondence table 351 is stored in the storage 35.

FIG. 3 shows a data configuration example of the correspondence table 351.

In the correspondence table 351, the imaging guide patterns for instructing predetermined motions to subjects at a time of imaging by the imaging device 50, and analysis contents are associated with each other and stored in predetermined words that can be included in the imaging orders. The predetermined word includes at least one of an imaging site, a disease, and an analysis content of a moving image obtained by the imaging device 50. Further, in the correspondence table 351, the predetermined words are classified into a disease, a breathing pattern, analysis, an orthopedic field and the like.

The imaging order includes patient information (a patient ID, a patient name, height, weight, age, sex, etc.), inspection information (an inspection ID, inspection date, an imaging site (a thoracic front, thoracic side, knee, wrist, etc.)), a disease (COPD, pulmonary embolism, asthma, fracture, etc.), and analysis contents (ventilation analysis, blood flow analysis, thoracic diaphragm moving amount measurement, etc.).

The imaging order may include information directly instructing the imaging guide pattern (deep breathing, quiet breathing, breath holding, etc.).

The imaging guide pattern refers to information for instructing a predetermined motion to a subject at a time of imaging, in which a series of motions that should be performed by the subject is set along a lapse of time. That is, the imaging guide pattern urges the subject to execute each motion at a timing at which each motion should be performed. The imaging guide pattern may be voice data for instructing a predetermined motion by voice, or may be video data for instructing a predetermined motion by video (moving image). Further, the imaging guide pattern may be information in which text data and image data for instructing a predetermined motion by displaying letters and images and display timing are associated with each other. The imaging guide pattern preferably includes a voice and an image for notifying an end of imaging in addition to the contents for instructing motions.

As the imaging guide pattern, for example, a breathing pattern for instructing breathing motions (thoracic pattern), an orthopedic pattern for instructing motions for imaging of orthopedics and the like are cited.

The breathing pattern includes a deep breathing pattern, a quiet breathing pattern, a breath holding (inhalation) pattern, and a breath holding (exhalation) pattern. As the breathing patterns, there can be patterns that differ in not only the order of "inhaling air", "exhaling air", "holding a breath" and the like but also in the continuation time and interval of the respective motions. For example, in the deep breathing pattern and the quiet breathing pattern, the number of times, speed, the magnitude of the load and the like of breathing may be divided stepwise. Further, in the breath holding pattern, a time of inhaling/exhaling/holding and the like, an exhaling position, an inhaling position and the like may be divided stepwise.

The orthopedic pattern includes a temporomandibular joint pattern, a knee joint pattern, a cervical spine pattern, and a wrist pattern. In motions of bending and stretching of a joint and holding and opening of hands of the orthopedic pattern, the number of times, a speed, a magnitude of load and the like may be divided stepwise.

The ventilation analysis obtains a periodic signal change amount that is synchronized with breathing, from thoracic moving images. The ventilation analysis is used in diagnosis by visualizing a local breathing function based on the ventilation analysis result.

The blood flow analysis obtains a degree of similarity of a signal change synchronized with a heart beat from the thoracic moving images. The blood flow analysis is used in diagnosis of a pulmonary vascular disease by visualizing a blood flow function based on the blood flow analysis result.

The thoracic diaphragm moving amount measurement automatically tracks movement of a thoracic diaphragm from thoracic moving images. A moving amount and a moving speed of the thoracic diaphragm are used in diagnosis of a lung disease.

In an analysis of a temporomandibular joint moving image, an analysis of tracking a moving distance of an incisor in time is performed.

In an analysis of a knee joint moving image, a moving distance of a contact point of a bent portion and a lateral condyle of a femur in extension of a knee joint and a superior articular surface of tibia is obtained.

In an analysis of a cervical spine moving image, arrangement of a vertebral body in a forward and backward bending movement of a cervical spine (cervical spine alignment) is analyzed in time series.

Priorities are set in advance for a plurality of predetermined words that can be included in the imaging order in the correspondence table 351. The priorities for the respective predetermined words are stored in the storage 35.

FIG. 4 shows a voice output example of the imaging guide pattern. A plurality of imaging guide patterns are prepared in advance for each kind of breathing, for each imaging site of the orthopedic field, and the like.

The controller 31 acquires the imaging order to imaging by the imaging device 50 from the RIS server 10 via the communicator 34.

The controller 31 extracts a predetermined word from the acquired imaging order, and selects the imaging guide pattern associated with the extracted predetermined word from the imaging guide pattern stored in the storage 35.

The controller 31 transmits the selected imaging guide pattern to the motion instruction device 40 via the communicator 34.

[Configuration of Motion Instruction Device]

FIG. 5 shows a functional configuration of the motion instruction device 40.

As shown in FIG. 5, the motion instruction device 40 includes a controller 41, a communicator 42, a storage 43, and a motion instruction outputter 44.

The controller 41 includes a CPU and a RAM, and generally controls processing operations of respective components of the motion instruction device 40. Specifically, the CPU of the controller 41 reads a system program and various processing programs that are stored in the storage 43, expands the programs in the RAM, and executes various kinds of processes in accordance with the expanded programs.

The communicator 42 performs data communication with the console 30.

The storage 43 includes a non-volatile semiconductor memory, or a hard disk. The storage 43 stores various programs executed in the controller 41, parameters necessary to execute the processes by the programs and data of processing results and the like.

The motion instruction outputter 44 is an instructor that instructs a predetermined motion to a subject based on the imaging guide pattern received from the console 30. For example, the motion instruction outputter 44 includes a speaker that outputs a voice, a monitor such as an LCD that displays an image, and a lamp (indoor light, illumination equipment, etc.), and instructs a predetermined motion to the subject by outputting a voice, displaying various images or emitting light in accordance with an instruction of a control signal inputted from the controller 41.

While the motion instruction outputter 44 is required to be close to a subject, the other components of the motion instruction device 40 do not necessarily have to be close to the subject.

[Operation of Radiation Imaging System]

Next, an operation in the radiation imaging system 100 is described.

FIG. 6 is a ladder chart showing an imaging process executed in the console 30 and the motion instruction device 40.

First, in the console 30, the controller 31 acquires the imaging order to imaging by the imaging device 50 from the RIS server 10 via the communicator 34 (step S1).

Next, the controller 31 extracts predetermined words from the acquired imaging order (step S2). Specifically, the controller 31 extracts the words (the imaging site, disease, analysis content, etc.) registered in advance in the correspondence table 351 of the storage 35 from the imaging order.

Next, the controller 31 refers to the correspondence table 351, and selects the imaging guide pattern and the analysis content that are associated with the extracted predetermined words (step S3). When a plurality of predetermined words are extracted from the imaging order, the controller 31 selects the imaging guide pattern and the analysis content that are associated with the predetermined word with a highest priority out of the plurality of predetermined words that are extracted.

Next, the controller 31 transmits the selected imaging guide pattern to the motion instruction device 40 via the communicator 34 (step S4).

In the motion instruction device 40, the controller 41 receives the imaging guide pattern transmitted from the console 30 via the communicator 42 (step S5). The controller 41 causes the storage 43 to store the received imaging guide pattern.

In the imaging room R3, a subject is on standby in an imaging position.

When a radiographer operates the operation unit 32 in the console 30 of the operation room R2, and brings the hand switch 321 into an on state, in a state where the subject is ready, the controller 31 transmits an imaging start instruction to the motion instruction device 40 and the imaging device 50 via the communicator 34 (step S6).

When the controller 41 receives the imaging start instruction from the console 30 via the communicator 42 in the motion instruction device 40, the controller 41 controls the motion instruction outputter 44 and causes the motion instruction outputter 44 to instruct a motion at the time of imaging, based on the imaging guide pattern (step S7). Specifically, the controller 41 causes a voice urging a predetermined motion to be outputted from a speaker, causes a monitor to display an image urging the predetermined motion, or causes a lamp to emit light to notify a motion timing.

The subject performs the predetermined motion in response to the motion instruction outputted from the motion instruction outputter 44. For example, the subject performs a breathing motion (inhaling/exhaling/holding), or performs bending and stretching the imaging site, or change of an orientation of the imaging site in response to the motion instruction.

In the imaging device 50, the subject is irradiated with radiation and imaging of moving images is performed. Specifically, the radiation irradiation control device 51 causes the radiation image generator 53 to generate image data of radiation images while controlling irradiation of radiation in the radiation source 52.

In the console 30, the controller 31 acquires moving image data from the imaging device 50 (step S8).

Next, the controller 31 performs analysis to the moving image data based on the analysis content selected in step S3 (step S9). When the analysis content corresponding to the predetermined word extracted from the imaging order is not set in the correspondence table 351, analysis is not performed.

Next, the controller 31 transmits the moving image data and the analysis result to the image management server 20 (step S10). The image management server 20 associates the moving image data and the analysis result with the patient and stores the moving image data and the analysis result.

The imaging process ends here.

As a preliminary practice mode, a subject may be allowed to check the imaging guide pattern in advance by the motion instruction outputter 44 outputting the motion instruction based on the imaging guide pattern in a state where radiation is not irradiated. Specifically, as the motion instruction, a voice is outputted from the speaker, or the instruction content is displayed on the monitor disposed in a position visible from the subject.

For example, when a thoracic moving image following a breathing motion is imaged, a breathing rhythm is presented to the subject by displaying a video recording a motion at the time of imaging, animation matched to breathing or the like. The subject repeats a breathing motion following the motion instruction like this several times, and thereby can learn the breathing pattern suitable for imaging in a short time.

Further, the imaging guide pattern for preliminary practice is transmitted to the tablet terminal 60 from the console 30, and the operation instruction is outputted by the voice outputter or a display of the tablet terminal 60, whereby the subject is allowed to practice the motion before imaging. A doctor or a radiographer gives the tablet terminal 60 to the subject, and the subject checks the imaging guide pattern before imaging by using the tablet terminal 60 and practices the motion in the time of imaging, outside the imaging room R3 or the like.

[Specific Examples of Breathing Pattern]

Referring to FIGS. 7 to 9, specific examples of the breathing pattern is described. In each of FIGS. 7 to 9, an ON/OFF state of the hand switch 321 of the console 30, a voice which is outputted by an auto voice function of the motion instruction outputter 44, a radiation pulse irradiated by the radiation source 52, and a thoracic diaphragm level by breathing of the subject are shown along a time axis.

FIG. 7 is a specific example of a breathing pattern at a time of deep breathing (with breath holding). When the radiographer brings the hand switch 321 into an ON state (one-step depression), a voice instructing an inhaling motion, a voice instructing a breath holding motion, a voice instructing an exhaling motion, a voice instructing a breath holding motion, a voice instructing an inhaling motion, and a voice notifying the end of imaging are outputted at predetermined timings from the motion instruction outputter 44. The subject takes a deep breath in accordance with the auto voice (voice guide). When the radiographer brings the hand switch 321 into a state further depressed (two-step depression) five seconds after the hand switch 321 is depressed one step (in the state where the subject has breathed deeply), irradiation of radiation is started by the radiation source 52. Further, at a timing at which a voice saying "OK, imaging is over." is outputted by the motion instruction outputter 44, the radiographer brings the hand switch 321 into an OFF state, and thereby irradiation of radiation by the radiation source 52 is stopped. In the imaging device 50, moving image data (from start of irradiation of radiation to turning off of the hand switch) at the time of deep breathing (with breath holding) is obtained.

FIG. 8 is a specific example of a breathing pattern at a time of quiet breathing. The radiographer urges the subject to breathe as usual. When the radiographer brings the hand switch 321 into an ON state (two-step depression), irradiation of radiation is started by the radiation source 52. The subject breathes as usual. For 15 seconds from the start of irradiation of radiation, no voice is outputted by the motion instruction outputter 44, and thereafter, at a timing at which the voice saying "OK, imaging is over." is outputted by the motion instruction outputter 44, the radiographer brings the hand switch 321 into an OFF state, whereby irradiation of radiation by the radiation source 52 is stopped. In the imaging device 50, moving image data at a time of quiet breathing (from the start of irradiation of radiation to turning off of the hand switch) is obtained.

FIG. 9 is a specific example of a breathing pattern at a time of breath holding (inhaling). When the radiographer brings the hand switch 321 into an ON state (one-step depression), a voice instructing an inhaling motion, a voice instructing a breath holding motion, a voice instructing a relax motion, and a voice notifying the end of imaging are outputted at predetermined timings by the motion instruction outputter 44. The subject holds breath and the like in accordance with the auto voice (voice guide). When the radiographer brings the hand switch 321 into a state further depressed (two-step depression) three seconds after the hand switch 321 is depressed one step (in a state where the subject is on the way to inhale lightly), irradiation of radiation is started by the radiation source 52. Further, at a timing at which the voice saying "OK, imaging is over." is outputted by the motion instruction outputter 44, the radiographer brings the hand switch 321 into an OFF state, and thereby irradiation of radiation by the radiation source 52 is stopped. In the imaging device 50, moving image data (from start of irradiation of radiation to turning off of the hand switch) at the time of holding breath (inhaling) is obtained.

As described above, according to the present embodiment, the imaging guide pattern which is associated with the predetermined word extracted from the imaging order is automatically selected, so that a selection error of the imaging guide pattern is prevented, and imaging of the moving images intended by the doctor can be achieved. Accordingly, it becomes possible to obtain the analysis result intended by the doctor by analyzing the obtained moving images.

For example, the imaging guide pattern for causing the breathing motion to be performed, and the imaging guide pattern for causing the imaging site to be bent and stretched, or causing the imaging site to change an orientation can be selected.

Specifically, a word such as the imaging site, disease, or the analysis content of the moving image obtained by the imaging device 50 which is included in the imaging order is extracted, and the imaging guide pattern which is associated with the extracted word can be selected.

Further, priorities are set to the predetermined words extracted from the imaging order, whereby when a plurality of predetermined words are extracted from the imaging order, it becomes possible to select the imaging guide pattern which is associated with the predetermined word with the highest priority.

The description in the above described embodiment is an example of the radiation imaging system according to the present invention, and the present invention is not limited to the description. Detail components and detail operations of the respective devices which configure the system can be arbitrarily changed within the range without departing from the gist of the present invention.

For example, in the above described embodiment, the console 30 acquires the imaging order from the RIS server 10, but the imaging order may be directly inputted to the console 30.

Further, in the above described embodiment, in the console 30, analysis of the moving image data is performed, but an analysis device for performing analysis of the moving image data or a server or a workstation for analysis tool may be provided.

Further, in the above described embodiment, the correspondence (correspondence table 351) of the imaging order (input) and the imaging guide pattern (output) is stored in the console 30, but the correspondence of the imaging order and the imaging guide pattern may be stored in the motion instruction device 40, and the controller 41 of the motion instruction device 40 may select the imaging guide pattern corresponding to the imaging order. Further, the correspondence of the imaging order and the imaging guide pattern may be stored in the RIS terminal 11, or exclusive equipment for selecting the imaging guide pattern. Further, a doctor may be allowed to check the imaging guide pattern selected in any of the devices, with the RIS terminal 11.

Further, the radiographer can change the imaging guide pattern to be carried out by operating the console 30 or the motion instruction device 40.

Further, the imaging guide pattern may be allowed to be customized in accordance with the facility by newly creating the imaging guide pattern or editing the guide content in the console 30 and the motion instruction device 40. For example, the radiographer may be allowed to finely adjust the interval of the breaths (inhaling/exhaling/holding) of the breathing pattern, a total imaging time and the like in the console 30 by watching the state of a patient.

Further, based on the imaging order, the imaging guide pattern is selected, and imaging conditions (the distance, tube voltage, tube current, pulse width, total imaging time, etc.) in the imaging device 50 may be automatically switched.

Further, based on the imaging order, the imaging guide pattern is selected, and an imaging device (one of a standing posture imaging table, a lying posture imaging table, a portable cassette, and a visiting vehicle+portable cassette) associated with the imaging order in advance may be automatically selected.

Further, based on the imaging order, image processing associated with the site to be imaged in advance is automatically selected, and the selected image processing may be automatically applied to the image.

Further, irradiation of radiation in the radiation source 52 may be automatically ended in a time (15 seconds or the like), but setting such as finishing in three breaths or the like may be enabled. However, for safety, irradiation of radiation is stopped without fail in an upper limit time set in advance.

Further, quality (pitch) of the voice which is outputted from the motion instruction outputter 44 may be made changeable. For example, it is desirable to set the voice to a sound that can be easily heard according to subjects, such as each patient and each age.

Further, when the imaging guide is displayed by video by the motion instruction outputter 44, the video may be set to a color that can be easily seen by the patients, for each patient, according to color-vision deficiency, age, and the like.

Further, the imaging room R3 may be equipped with a plurality of speakers to which the motion instruction outputter 44 outputs voice guide, or a plurality of monitors to which the motion instruction outputter 44 outputs video guide. Further, the imaging room R3 and the operation room R2 may be each equipped with a speaker and a monitor.

Further, in the above described embodiment, the case where the speaker which notifies the subject of the motion timing through auditory sense, and the monitor, the lamp or the like which notifies the subject of the motion timing through the sense of sight are used is described as the motion instruction outputter 44 (instructor), a vibrator, a fan or the like that notifies the subject of the motion timing through tactual sense may be used. Further, a plurality of instructors may be combined. Specifically, when the motion is instructed by a combination of a voice and an image, the timing of motion is easily reported to the subject.

Further, when the motion instruction outputter 44 displays a video, a target breathing pattern and a present state of breathing of the subject may be displayed by a change with time of an inhaling amount or the like. The subject checks the target breathing pattern and the present state of breathing, and thereby can bring the breathing motion of the subject himself or herself close to the target pattern.

Further, in accordance with the motion instruction content, the radiation irradiation control device 51 may control the amount of radiation that is irradiated by the radiation source 52. Alternatively, the breathing state of a subject is monitored, and the radiation amount may be controlled in accordance with information on the breathing state. For example, the amount of radiation is increased at the times of a maximum exhalation position and a maximum inhalation position, and the amount of radiation is decreased in the other period.

Further, the motion instruction outputter 44 may be directly connected to the console 30, and the console 30 may control the motion instruction outputter 44. Further, the motion instruction outputter 44 is connected to the radiation irradiation control device 51, and the radiation irradiation control device 51 may control the motion instruction outputter 44.

Further, a function of checking whether or not the imaging result (moving image data) obtained by imaging the subject is within an allowable range of diagnosis and analysis may be included.

Here, a breathing motion instruction is described as an example. When a radiographer instructs start of radiation imaging from the operation unit 32 of the console 30, the controller 41 of the motion instruction device 40 causes a breathing motion instruction (guidance) to be outputted from the motion instruction outputter 44, and the subject breathes in accordance with the motion instruction. After several times of breathing with which the patient gets accustomed to the rhythm of breathing, imaging of the thoracic moving image following a breathing motion for one period is executed by the imaging device 50. The controller 31 of the console 30 extracts a lung field part from the thoracic moving image, and determines whether or not the thoracic moving image is within an allowable range from the change with time of the lung field part. For example, when abnormal movement of parameters that can show a dynamic state of breathing such as a lung field length, and a lung field area, and a result deviating from a threshold are obtained, the imaging is determined as improper (outside the allowable range). When the imaging is within the allowable range, the thoracic moving image is stored as an imaging result, and when the imaging is outside the allowable range, warning and reimaging are reported.

Further, propriety of the imaging result may be checked based on movement of the thoracic diaphragm.

Further, an emergency stop button for forcefully interrupting irradiation of radiation in the radiation source 52 may be provided. In this case, when the subject finds it difficult to continue imaging due to pain in the imaging site during imaging, imaging can be stopped by depressing the emergency stop button.

Further, when a doctor selects a patient and issues an imaging order from the RIS terminal 11, the doctor may ask the RIS server 10 whether or not an implementation history of radiation imaging of the patient of the past is available, and when the implementation history is available, same imaging as the past may be automatically ordered. Alternatively, when the implementation history of radiation imaging of the patient of the past is available, the doctor may select any order from the past orders, and may issue an imaging order for performing the same imaging as the selected order.

Although embodiments of the present invention have been described and illustrated in detail, the disclosed embodiments are made for purposes of illustration and example only and not limitation. The scope of the present invention should be interpreted by terms of the appended claims.

The entire disclosure of Japanese Patent Application No. 2018-099252, filed on May 24, 2018, is incorporated herein by reference in its entirety.

What is claimed is:

1. A radiation imaging system including an imager that performs imaging of moving images by irradiating a subject with radiation, the radiation imaging system comprising:
    a storage in which a plurality of imaging guide patterns are stored, each of the plurality of imaging guide patterns instructing a respective predetermined motion to the subject at a time of imaging by the imager, the plurality of imaging guide patterns being stored in association with respective predetermined words;

a hardware processor that acquires an imaging order for imaging by the imager from a Radiology Information System (RIS) server, the imaging order including instructions for obtaining images of the subject, wherein the hardware processor further extracts at least one word of the predetermined words from the acquired imaging order, and selects an imaging guide pattern that is associated with the extracted at least one word from the plurality of imaging guide patterns stored in the storage; and an instructor that instructs the predetermined motion to the subject, based on the selected imaging guide pattern.

2. The radiation imaging system according to claim 1, wherein the predetermined motion is breathing.

3. The radiation imaging system according to claim 1, wherein the predetermined motion is bending and stretching of an imaging site, or change of an orientation of the imaging site.

4. The radiation imaging system according to claim 1, wherein the extracted at least one word includes at least one of an imaging site, a disease, and an analysis content of a moving image obtained by the imager.

5. The radiation imaging system according to claim 1, wherein the instructor instructs the predetermined motion by outputting a voice.

6. The radiation imaging system according to claim 1, wherein the instructor instructs the predetermined motion by displaying an image.

7. The radiation imaging system according to claim 1, wherein priorities are set to the respective predetermined words stored in the storage, and when the at least one word is a plurality of words that are extracted from the imaging order, the hardware processor selects an imaging guide pattern that is associated with one extracted word among the plurality of words with a highest priority.

8. The radiation imaging system according to claim 1, wherein the predetermined words in the storage are classified into classifications related to categories of data included in the imaging order.

9. An imaging guide pattern selection device comprising:

a storage in which a plurality of imaging guide patterns are stored, each of the plurality of imaging guide patterns instructing a respective predetermined motion to a subject at a time of imaging by an imager that performs imaging of moving images by irradiating the subject with radiation, and each of the plurality of imaging guide patterns being stored in association with a respective predetermined word; and a hardware processor that acquires an imaging order for imaging by the imager from a Radiology Information System (RIS) server, the imaging order including instructions for obtaining images of the subject, wherein the hardware processor further extracts at least one word of the predetermined words from the acquired imaging order, and selects an imaging guide pattern that is associated with the extracted at least one word from the plurality of imaging guide patterns stored in the storage, and transmits the selected imaging guide pattern to a motion instruction device that instructs the predetermined motion to the subject based on the selected imaging guide pattern.

* * * * *